United States Patent
Troy et al.

(10) Patent No.: US 9,488,589 B2
(45) Date of Patent: Nov. 8, 2016

(54) MAPPING DAMAGED REGIONS ON OBJECTS

(71) Applicant: The Boeing Company, Chicago, IL (US)

(72) Inventors: James J. Troy, Issaquah, WA (US); Scott W. Lea, Renton, WA (US); Susan H. Young, Seattle, WA (US)

(73) Assignee: The Boeing Company, Chicago, IL (US)

( * ) Notice: Subject to any disclaimer, the term of this patent is extended or adjusted under 35 U.S.C. 154(b) by 269 days.

(21) Appl. No.: 14/066,658

(22) Filed: Oct. 29, 2013

(65) Prior Publication Data

US 2015/0116481 A1    Apr. 30, 2015

(51) Int. Cl.
| | |
|---|---|
| *B64F 5/00* | (2006.01) |
| *G01N 21/88* | (2006.01) |
| *G01S 17/89* | (2006.01) |
| *G01B 11/24* | (2006.01) |
| *G01S 17/42* | (2006.01) |

(52) U.S. Cl.
CPC ............. *G01N 21/88* (2013.01); *B64F 5/0045* (2013.01); *G01B 11/24* (2013.01); *G01S 17/42* (2013.01); *G01S 17/89* (2013.01)

(58) Field of Classification Search
CPC ............................ B64F 5/0045; G01N 21/88
USPC ........................................................ 348/128
See application file for complete search history.

(56) References Cited

U.S. PATENT DOCUMENTS

| 4,974,261 A * | 11/1990 | Nakahara ............... G01N 21/88 348/128 |
| --- | --- | --- |
| 7,298,152 B1 * | 11/2007 | Wilke .................. G07C 5/0808 324/639 |
| 7,859,655 B2 | 12/2010 | Troy et al. |
| 8,044,991 B2 | 10/2011 | Lea et al. |
| 2009/0086199 A1 * | 4/2009 | Troy ........................ G01C 1/04 356/251 |
| 2009/0138233 A1 | 5/2009 | Kludas et al. |
| 2010/0250148 A1 | 9/2010 | Meredith et al. |
| 2014/0184786 A1 * | 7/2014 | Georgeson ......... G01N 21/8851 348/128 |
| 2014/0267778 A1 * | 9/2014 | Webb .................. H04N 5/2328 348/169 |

FOREIGN PATENT DOCUMENTS

WO    2013112229 A1    8/2013

OTHER PUBLICATIONS

U.S. Patent application (non-published), U.S. Appl. No. 12/897,408, filed Oct. 4, 2010, James J. Troy and Scott Lea.

* cited by examiner

*Primary Examiner* — Jeffery Williams (74) *Attorney, Agent, or Firm* — Duft Bornsen & Fettig, LLP

(57) ABSTRACT

Systems and methods for mapping a damaged region on an object. An exemplary system captures an image of the damaged region with a camera, selects target points around a boundary of the damaged region on the image, and determines 2D image coordinates for the target points on the image. The system further determines angles for aiming a laser ranging device at each of the target points based on the image coordinates, and measures a distance to each of the target points with the laser ranging device based on the aiming angles. The system then calculates 3D coordinates for each of the target points in the coordinate system of the object based on the distance measurement and the 2D image coordinates for each of the target points.

17 Claims, 10 Drawing Sheets

MAPPING DAMAGED REGIONS ON OBJECTS

FIELD

This disclosure relates to the field of non-destructive inspection and repair or maintenance of objects, such as aircraft.

BACKGROUND

When an aircraft or another type of machine is damaged, maintenance crews are tasked with inspecting and repairing the damage. For example, the fuselage of an aircraft may be dented or damaged by heat. When this occurs, the maintenance crew typically measures the size, shape, and location of the damaged region. The crew then determines if a repair is needed, and helps design a repair process. Conventionally, the measurements are taken by hand with a tape measure or ruler. Newer techniques allow the maintenance crew to measure the damaged region using non-destructive inspection techniques. After the analysis, a maintenance crew performs whatever repair is deemed appropriate for the damage.

However, after the damaged region is repaired, the exact location of the damage may not be evident in the future. The repair may be covered by paint or otherwise concealed so that the location of the prior repair is not visible. This may hinder the maintenance crew in correctly analyzing what types of future repairs are needed on the aircraft. For example, if a section of the aircraft's wing was previously repaired and new damage occurs proximate to the location of the previous repair, then a maintenance crew may utilize different repair processes if they were aware of the previous repair. However, the precise location of the previous repair may not be documented in a way that allows the maintenance crew to determine if the present damage is in the same location as the previous repair.

SUMMARY

Embodiments described herein map a damaged region on an object, such as an aircraft, into a known coordinate system of the object so that the precise location of the damaged region is recorded for the object. A system as described herein uses a camera to capture a two-dimensional (2D) image of the damaged region. The system then selects target points on the 2D image, computes aiming angles, and measures a distance to the target points with a laser ranging device. The system then calculates three-dimensional (3D) coordinates for the target points in the coordinate system of the object based on the measurements from the laser range device. The 3D coordinates for the damaged region are then stored in a database for the object. The 3D coordinates can be used to model the damaged region for assessing the damage to the object, for determining an area/size of the damage, to identify which parts of the object may have been affected by the damage, etc. The model of the damaged region may also be used in the future to identify the precise location on the object that has sustained damage in the past.

One embodiment comprises an apparatus for mapping a damaged region on an object. The apparatus includes a measurement unit having a laser ranging device and a camera. The apparatus also includes a controller coupled to the measurement unit. The controller is configured to calibrate the measurement unit with respect to a coordinate system of the object. After calibration, the controller is configured to capture an image of the damaged region with the camera, to select target points around a boundary of the damaged region based on the image, and to determine 2D image coordinates (e.g. pixel coordinates) for the target points on the image. The controller is further configured to determine angles (e.g., pan and tilt) for aiming the laser ranging device at each of the target points based on the 2D image coordinates, and to measure a distance to each of the target points with the laser ranging device based on the angles. The controller is further configured to calculate 3D coordinates for each of the target points in the coordinate system of the object based on the distance measurement and the 2D image coordinates for each of the target points.

Another embodiment comprises a method for mapping a damaged region on an object. The method includes calibrating a measurement unit with respect to a coordinate system of the object, where the measurement unit includes a laser ranging device and a camera. After calibration, the method further includes capturing an image of the damaged region with the camera, selecting target points around a boundary of the damaged region based on the image, and determining 2D image coordinates for the target points on the image. The method further includes determining angles for aiming the laser ranging device at each of the target points based on the 2D image coordinates, and measuring a distance to each of the target points with the laser ranging device based on the angles. The method further includes calculating 3D coordinates for each of the target points in the coordinate system of the object based on the distance measurement and the 2D image coordinates for each of the target points.

The features, functions, and advantages that have been discussed can be achieved independently in various embodiments or may be combined in yet other embodiments, further details of which can be seen with reference to the following description and drawings.

DESCRIPTION OF THE DRAWINGS

Some embodiments of the present invention are now described, by way of example only, with reference to the accompanying drawings. The same reference number represents the same element or the same type of element on all drawings.

DESCRIPTION

The figures and the following description illustrate specific exemplary embodiments. It will be appreciated that those skilled in the art will be able to devise various arrangements that, although not explicitly described or shown herein, embody the principles described herein and are included within the contemplated scope of the claims that follow this description. Furthermore, any examples described herein are intended to aid in understanding the principles of the disclosure, and are to be construed as being without limitation. As a result, this disclosure is not limited to the specific embodiments or examples described below, but by the claims and their equivalents.

Figure 1:
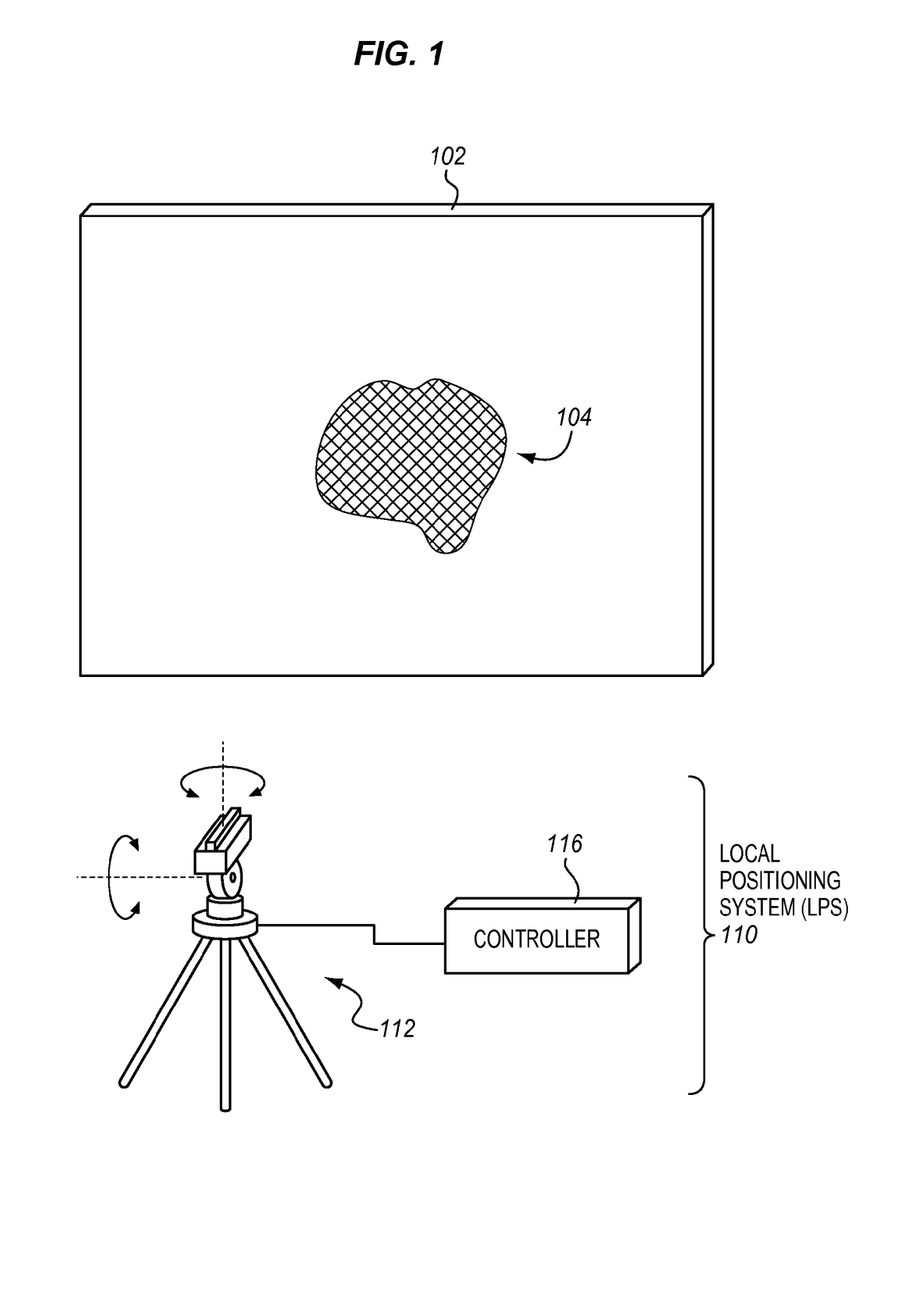
FIG. 1 illustrates a local positioning system (LPS) in an exemplary embodiment.

FIG. 1 illustrates a local positioning system (LPS) 110 in an exemplary embodiment. LPS 110 is a system that is able to measure 3D position, such as the location of damage on an object 102. For instance, FIG. 1 shows a damaged region 104 on object 102. The damage may be a dent or puncture from impact of a foreign object, may be heat damage, may be a scratch or abrasion, or any other type of damage. LPS 110 is able to measure surface positions of the damaged region 104, and map the measurements of the damaged region 104 into a known coordinate system for object 102. For example, assume that object 102 is a portion of an aircraft. An aircraft is typically modeled as a 3D CAD model within a known coordinate system. Thus, if damaged region 104 is located on a portion of the aircraft, then LPS 110 is able to map the damaged region 104 to the known coordinate system for the aircraft.

LPS 110 includes a measurement unit 112 and a controller 116. As will be further shown in FIG. 2, measurement unit 112 includes a laser ranging device and a camera. The laser ranging device and camera are mounted on a 2-axis gimbal assembly so that the viewing angle of the camera can be adjusted, and the laser ranging device can be aimed at specific points on object 102. Controller 116 comprises any component or device that is able to process data from measurement unit 112 to map the damaged region 104 to a coordinate system of object 102. Controller 116 is connected to measurement unit 112 through some type of communication medium, such as a wired connection or wireless connection.

Figure 2:
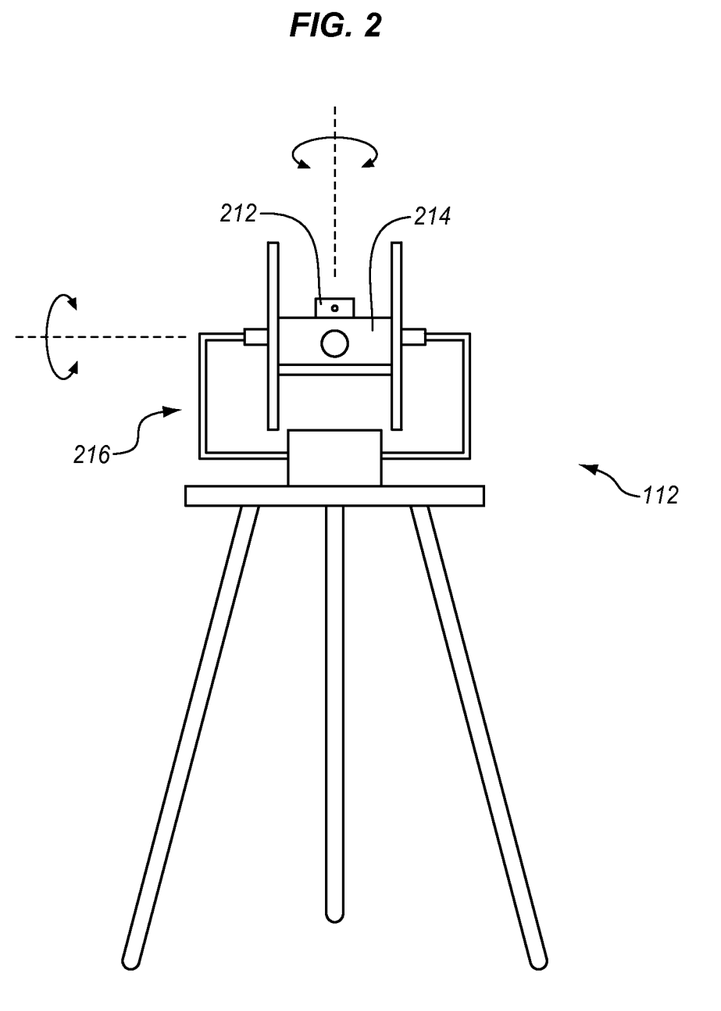
FIG. 2 illustrates a measurement unit of a local positioning system (LPS) in an exemplary embodiment.

FIG. 2 illustrates measurement unit 112 of LPS 110 in an exemplary embodiment. Measurement unit 112 includes a laser ranging device 212 and a camera 214 mounted on a two-axis gimbal assembly 216. Laser ranging device 212 comprises any component or module that uses a laser projector to measure the distance between the projector and an object. Camera 214 comprises any type of camera that captures digital images. Because laser ranging device 212 and camera 214 are mounted on gimbal assembly 216, the angles at which laser ranging device 212 and camera 214 are pointed during measurements can be precisely controlled and measured. Although not specifically shown in FIG. 2, measurement unit 112 may further include rotary motors that control the movement of gimbal assembly 216, and rotary encoders that determine the mechanical position of gimbal assembly 216.

To take measurements of damaged region 104, measurement unit 112 is mounted or positioned at a location with a clear line of sight to damaged region 104. An exemplary process for measuring damaged region 104 is described in FIG. 3.

Figure 3:
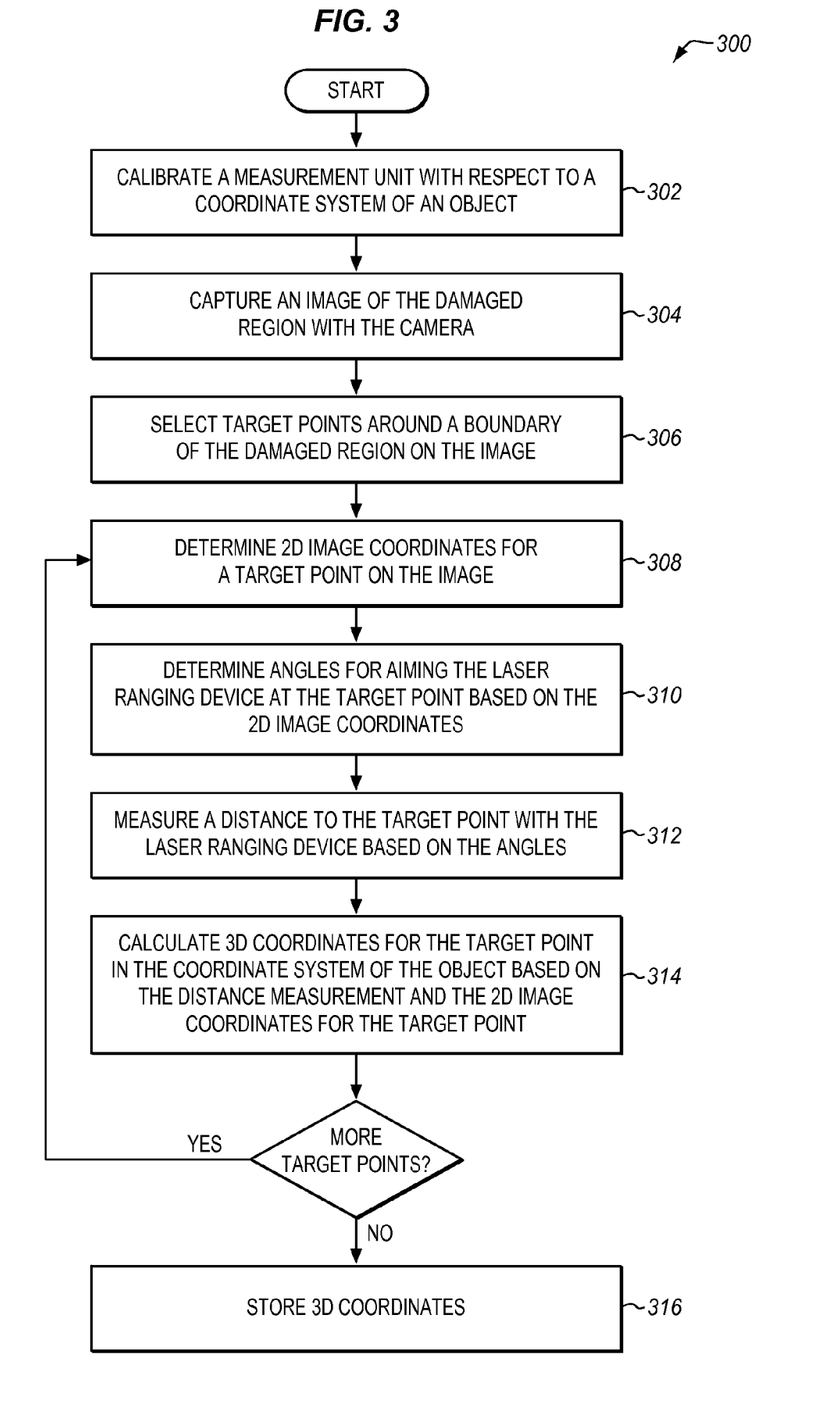
FIG. 3 is a flow chart illustrating a method for measuring a damaged region on an object in an exemplary embodiment.

FIG. 3 is a flow chart illustrating a method 300 for measuring a damaged region on object 102 in an exemplary embodiment. The steps of method 300 will be described with respect to LPS 110 of FIGS. 1-2, although one skilled in the art will understand that the methods described herein may be performed by other devices or systems not shown. The steps of the methods described herein are not all inclusive and may include other steps not shown. The steps for the flow charts shown herein may also be performed in an alternative order.

Figure 4:
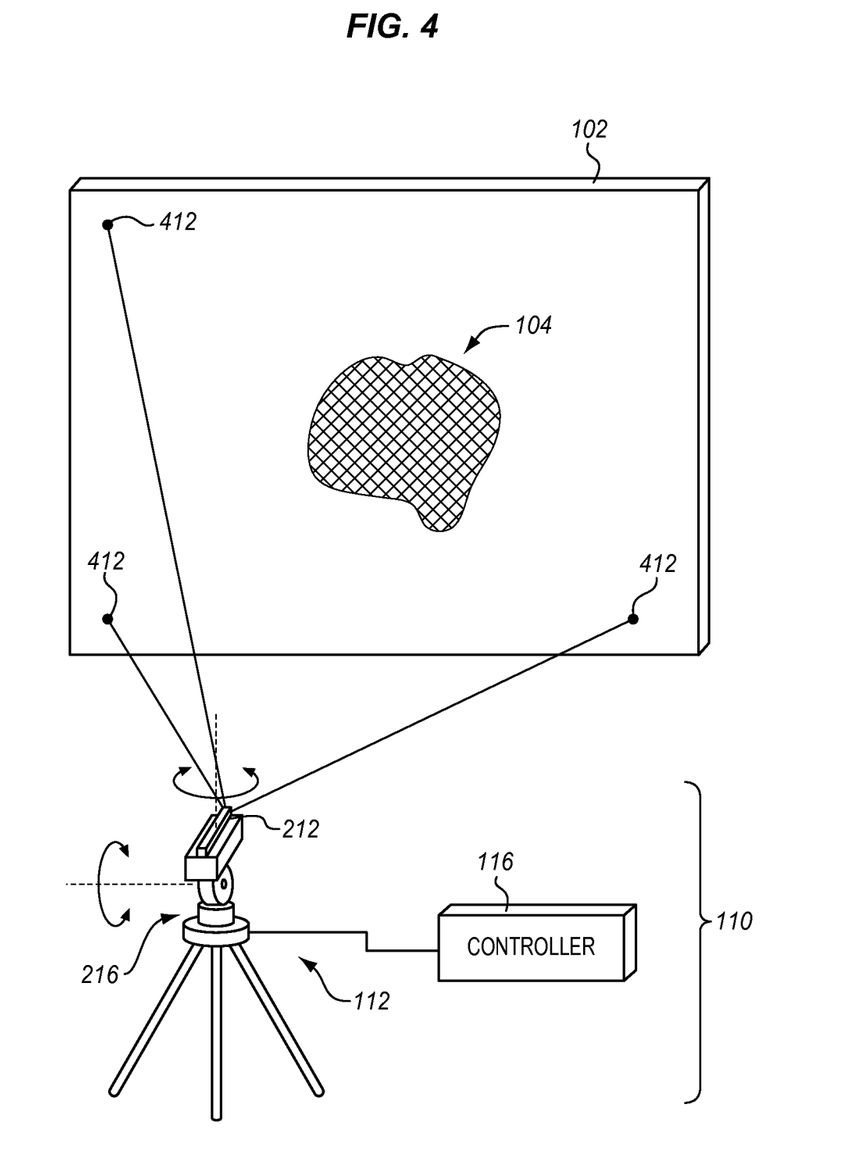
FIG. 4 illustrates a plurality of reference points on an object in an exemplary embodiment.

To begin, controller 116 calibrates measurement unit 112 of LPS 110 with respect to the coordinate system of object 102 in step 302. To do so, controller 116 aims laser ranging device 212 at a plurality of reference points on object 102. The reference points are visible features that have known locations in the coordinate system of object 102. For example, if object 102 is an aircraft, then a reference point may be a corner of a window, a tip of a wing, etc. FIG. 4 illustrates a plurality of reference points 412 on object 102 in an exemplary embodiment. Controller 116 aims laser ranging device 212 at each of the reference points 412, and laser ranging device 212 measures a distance to each of the reference points 412. Controller 116 also determines the angles in which laser ranging device 212 was aimed by gimbal assembly 216 at each of the reference points 412 (e.g., through the encoders on gimbal assembly 216). For example, when the rotary motors actuate the gimbal assembly 216 to aim laser ranging device 212 onto a reference point 412, controller 116 is able to determine the mechanical position of the rotary encoders connected to gimbal assembly 216 to determine the angle measurements (e.g., azimuth and elevation, or pan and tilt) for this reference point 412. Based on these measurements and the initial calibration of the system, controller 116 can calculate 3D (three-dimensional) coordinates for measurement unit 112 defined in the coordinate system of object 102. An exemplary process for calibrating LPS 110 is described in U.S. Pat. No. 7,859,655, which is incorporated by reference as if fully included herein.

The system calibration describes the relationship between the location of the measurement unit 112 and the coordinate system of object 102. This relationship can be stored as a 4×4 homogeneous transformation matrix, which is referred to herein as a calibration matrix. After this calibration matrix has been determined, any additional positions measured by LPS 110 can be multiplied by the calibration matrix to return results defined in the coordinate system of object 102.

Figure 5:
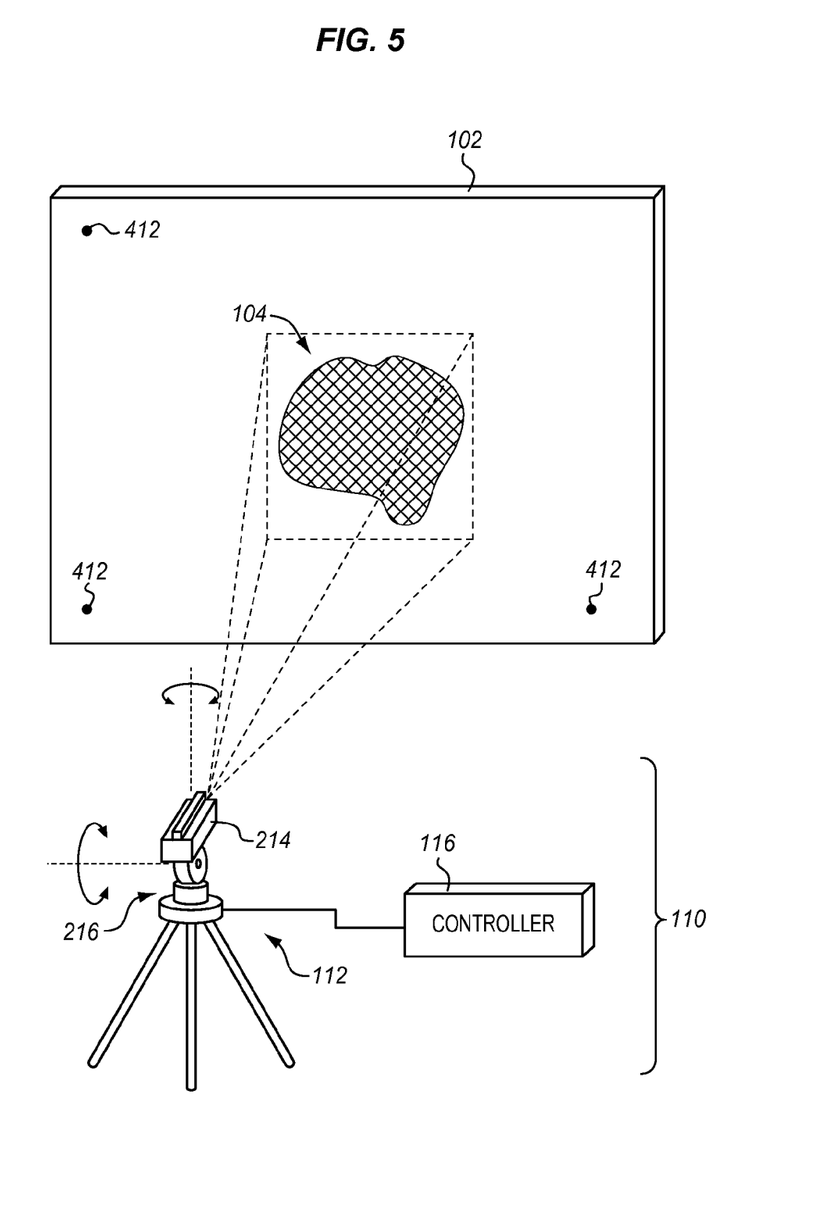
FIG. 5 illustrates a camera of a local positioning system (LPS) aimed toward a damaged region in an exemplary embodiment.

After calibration, LPS 110 can begin to measure the damaged region 104 of object 102. LPS 110 captures an image of the damaged region 104 with camera 214 in step 304 (see FIG. 3). To capture the image, controller 116 controls gimbal assembly 216 of measurement unit 112 to aim camera 214 toward the damaged region 104 to capture a digital image of damaged region 104. The image will be a 2D representation of the damaged region 104. FIG. 5 illustrates camera 214 aimed toward the damaged region 104 in an exemplary embodiment. The field of view of camera 214 is illustrated by dashed lines in FIG. 5.

Figure 6:
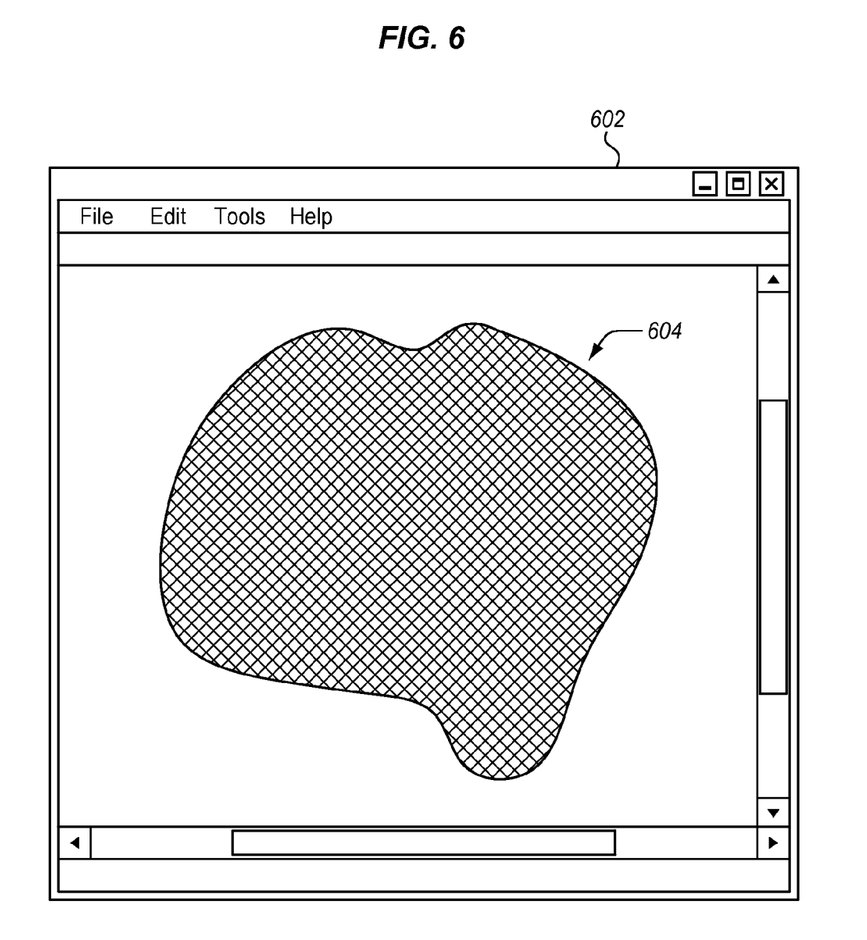
FIG. 6 illustrates a user interface screen displaying an image of a damaged region in an exemplary embodiment.

After capturing the image of the damaged region 104, controller 116 may load the image into an application or program that processes the image to create aiming positions for LPS 110 in order to acquire 3D points on object 102. For example, one type of application may provide a user interface that displays the image to a user. FIG. 6 illustrates a user interface screen 602 displaying an image 604 of the damaged region 104 in an exemplary embodiment. Although not specifically shown in FIG. 6, the application may also provide a number of tools for the user to manipulate the image 604.

Figure 7:
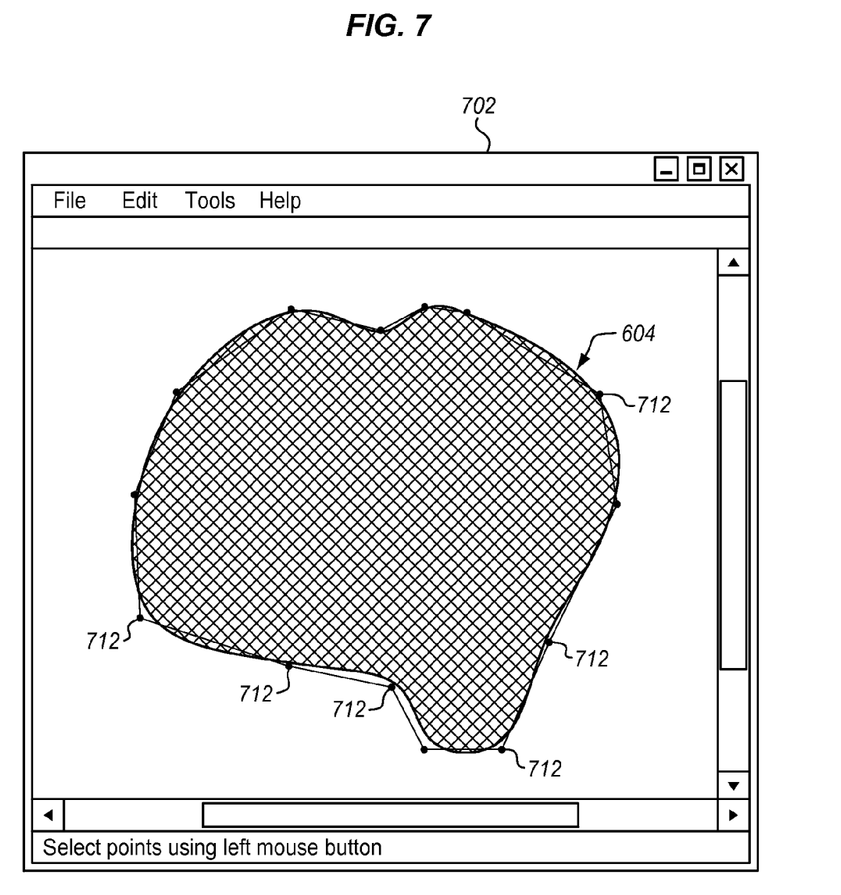
FIG. 7 illustrates a user interface screen displaying a plurality of target points defined around a boundary of a damaged region in an exemplary embodiment.

Controller 116 then selects one or more target points around a boundary of the damaged region 104 on the image 604 in step 306 (see FIG. 3). A target point is a specific location on object 102 that is designated for measurement by LPS 110. In the embodiments described herein, LPS 110 is configured to map the contour of the damaged region into the coordinate system of object 102. Therefore, LPS 110 selects or specifies the target points around the boundary of the damaged region 104 on the image 604, which will be measured in order to map the contour. The target points, also referred to as periphery target points, may be selected in a number of ways. In one embodiment, the target points may be manually selected by a user. For instance, the user may access the user interface screen 602 illustrated in FIG. 6 to enter one or more target points around the boundary of the damaged region 104 as depicted in the image 604, such as by using a mouse in an image editor. LPS 110 then receives input from the user selecting the target points around the boundary of the damaged region 104. In another embodiment, LPS 110 may use an edge detection program or some other application that determines the boundary of the damaged region 104 in image 604, and automatically selects one or more target points around the boundary of the damaged region 104. FIG. 7 illustrates a user interface screen 702 displaying a plurality of target points 712 defined around the boundary of the damaged region 104 in an exemplary embodiment.

Figure 8:
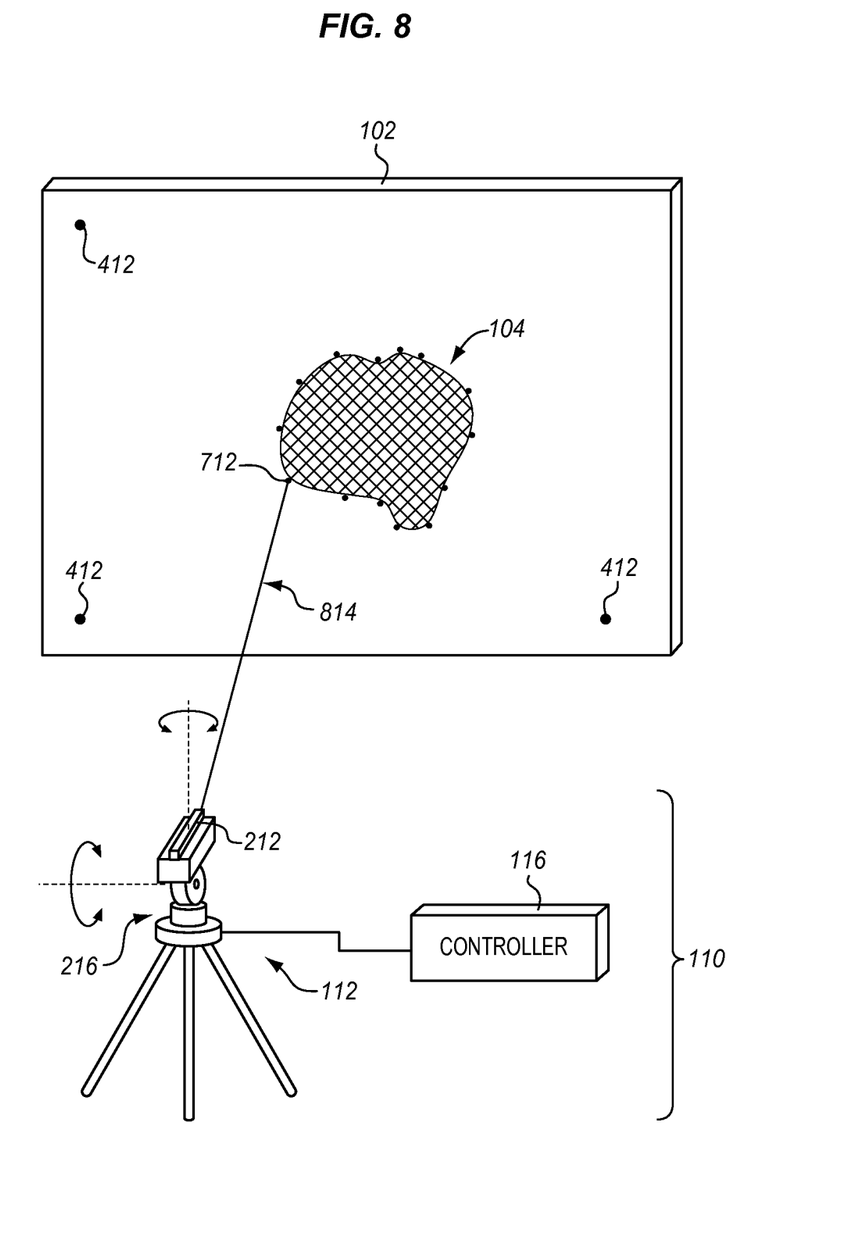
FIG. 8 illustrates a laser ranging device of a local positioning system (LPS) performing a distance measurement to a target point in an exemplary embodiment.

For each of the target points, LPS 110 may operate as follows. Controller 116 determines 2D image coordinates for a target point 712 on image 604 in step 308. Controller 116 then determines angles (e.g., elevation/azimuth or pan/tilt) for aiming laser ranging device 212 at the target point 712 based on the 2D image coordinates in step 310. The angles used for aiming laser ranging device 212 may be referred to herein as aiming angles or gimbal angles. After determining the aiming angles, controller 116 measures a distance to the target point 712 with laser ranging device 212 based on the aiming angles in step 312. For example, controller 116 may actuate the rotary motors of gimbal assembly 216 to aim laser ranging device 212 onto the target point 712 based on the aiming (e.g., pan and tilt) angles determined for this target point 712 (see also FIG. 2). FIG. 8 illustrates laser ranging device 212 performing a distance measurement to a target point 712 in an exemplary embodiment. Line 814 represents the laser from laser ranging device 212 being aimed at target point 712 to measure a distance to target point 712.

At this stage, controller 116 has data for the 2D image coordinates of the target point 712, the calibration matrix for LPS 110 (including the laser ranging device 212) that is defined with respect to the coordinate system of object 102, and a distance between laser ranging device 212 and the target point 712 on object 102. Thus, controller 116 can calculate 3D coordinates (e.g., Cartesian x, y, z coordinates) for the target point 712 in the coordinate system of object 102 based on the distance measurement for the target point 712 and the 2D image coordinates for the target point 712 in step 314. The 3D coordinates for the target point may be referred to as "system coordinates", as they are in the coordinate system of object 102.

LPS 110 repeats steps 308-314 for each of the target points 712 selected in step 306 to determine 3D coordinates. When 3D coordinates are determined for multiple target points around the boundary of the damaged region 104, this process maps the boundary of the damaged region 104 into the coordinate system of object 102. Thus, the location of the damaged region 104 is mapped into the coordinate system of object 102, as well as a shape or contour of the damaged region 104. LPS 110 may then store this data for the damaged region 104 in step 316, such as in a database. LPS 110 may store the raw 3D coordinates for the target points 712 in the database. LPS 110 may also store additional data in the database, such as an area/size of the damaged region 104 calculated from the 3D coordinates, a date/time the data was collected, a location of object 102 when the measurements were taken, etc.

Figure 9:
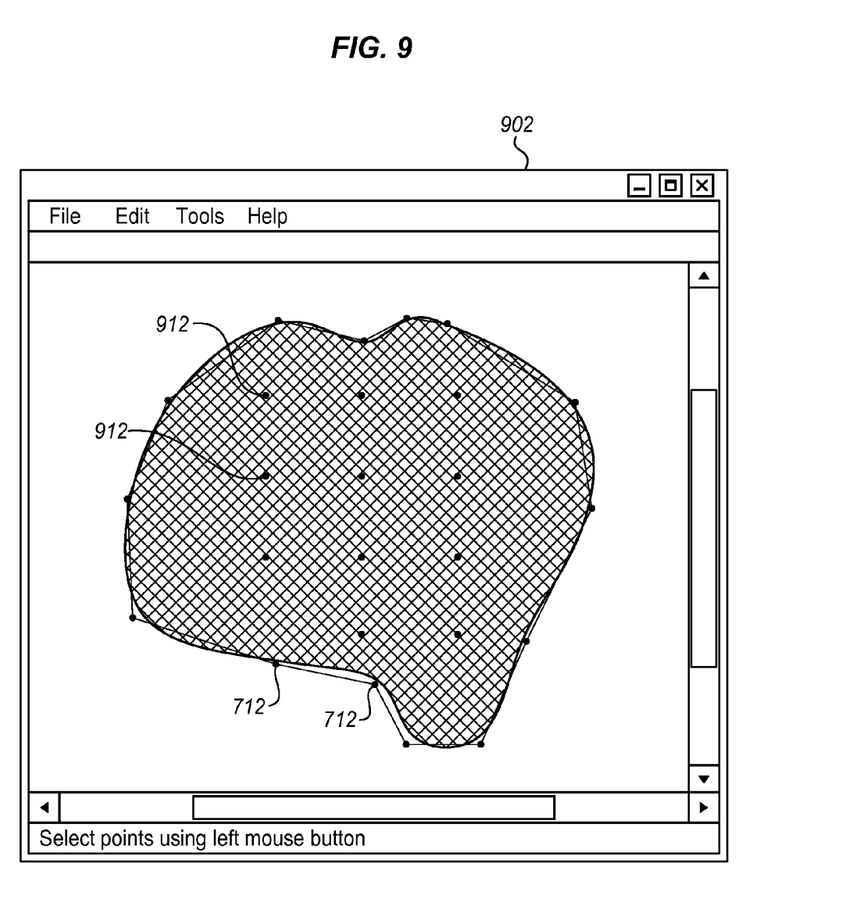
FIG. 9 illustrates a screen displaying a plurality of target points defined within a boundary of a damaged region in an exemplary embodiment.

In addition to defining target points along the boundary of the damaged region 104, LPS 110 may be used to measure additional target points within the boundary of the damaged region 104. FIG. 9 illustrates a user interface screen 902 displaying a plurality of target points 912 defined within a boundary of the damaged region 104 in an exemplary embodiment. The additional target points, also referred to as inner target points, may be selected in a number of ways. In one embodiment, the inner target points 912 may be manually selected by a user. For instance, the user may access the user interface screen 902 illustrated in FIG. 9 to enter one or more inner target points 912, such as by using a mouse. In another embodiment, LPS 110 may use a program or some other application that automatically selects a plurality or array of inner target points within the boundary of the damaged region 104. Whether manually or automatically selected, LPS 110 is used to measure these inner target points of damaged region 104, and determine 3D coordinates (e.g., x, y, z coordinates) for the inner target points 912 in the coordinate system of object 102 in steps 308-314 of FIG. 3. By determining 3D coordinates of the inner target points 912, the data stored for damaged region 104 will also indicate a surface contour of the damage (e.g., the depth of a dent) in addition to the location of the damaged region 104.

Figure 10:
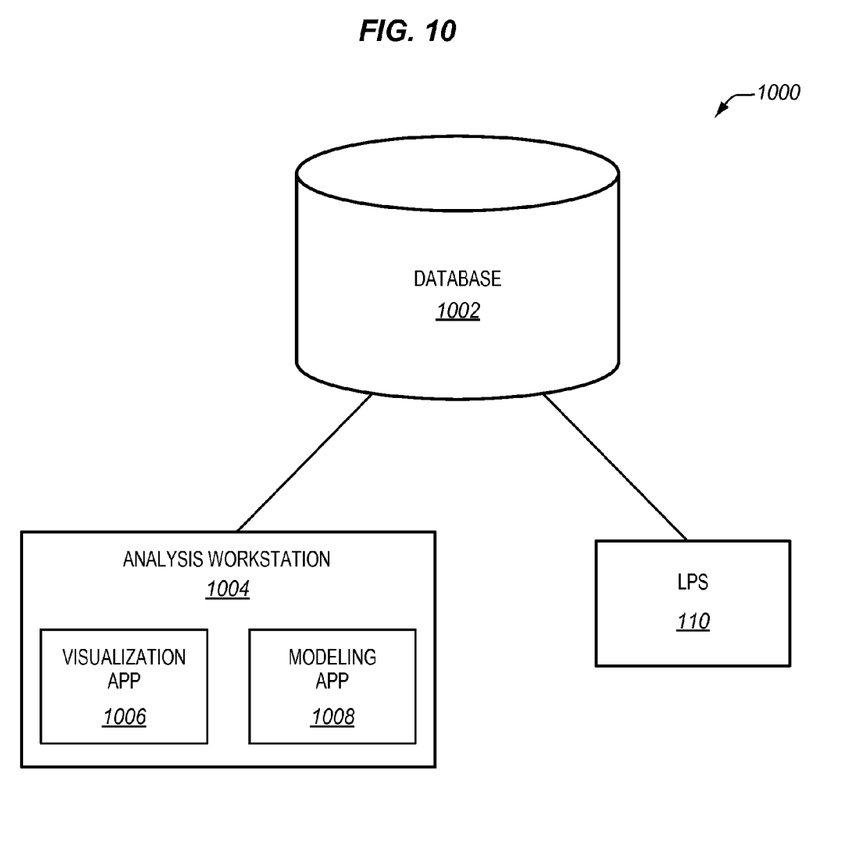
FIG. 10 illustrates a system for analyzing data for a damaged region of an object in an exemplary embodiment.

With the data for the damaged region 104 stored in a database, systems may be able to retrieve the data to analyze the damage to object 102. FIG. 10 illustrates a system 1000 for analyzing data for the damaged region 104 in an exemplary embodiment. System 1000 includes a database 1002 that stores data for the damaged region 104 of object 102 as described above. Database 1002 may also store additional data for other damaged regions on object 102 that were collected at the same time or another time as damaged region 104. System 1000 also includes an analysis workstation 1004 that is able to interface with database 1002. Analysis workstation 1004 comprises any system that executes one or more applications to process the data for damaged region. In one embodiment, analysis workstation 1004 includes a visualization application 1006 that is able to access database 1002 to retrieve the data for the damaged region 104 of object 102. The visualization application 1006 may also retrieve a 3D CAD model of object 102 from database 1002 or another database. The visualization application 1006 then processes the data for the damaged region 104 to generate a 3D representation (or model) of the damaged region 104, and depict the damaged region 104 on the 3D CAD model of object 102. Visualization application 1006 therefore is able to overlay the 3D representation of the damaged region 104 on the 3D CAD model of object 102. By overlaying the 3D representation of the damaged region 104 on the 3D CAD model of object 102, this shows the exact location of the damaged region 104 on object 102. Visualization application 1006 may also determine an area or an approximate size of the damaged region 104 based on the 3D representation, or otherwise process the data for the damaged region 104. Visually indicating the location of the damaged region 104 on a 3D CAD model of object 102 can assist a maintenance crew in accessing the severity of the damage, selecting repair processes for object 102, etc.

Analysis workstation 1004 (through visualization application 1006 or another application) may also determine which parts within object 102 may be affected by the damage based on the location of the damaged region 104. For example, showing the damaged region 104 in context with the 3D model of object 102 may help an analyst determine which parts below the surface may be damaged. Analysis workstation 1004 may also retrieve data for prior damage to object from database 1002. Based on the location of the damaged region 104 and any prior damage, analysis workstation 1004 may recommend a repair on object 102. For example, if there are delicate parts for the object 102 in the vicinity of the damaged region, analysis workstation 1004 may provide guidance or recommend that certain parts in this area of object 102 be repaired or inspected.

Visualization application 1006 may also have the ability to represent images as texture maps that can be applied (overlaid) on the 3D models. This allows photographs of the damaged region 104 captured with LPS 110 to be shown in context with the measured 3D points of the damaged region 104 and 3D CAD models of object 102. In order to be properly used as texture maps, the images would be perspective-adjusted (using the relative location of LPS 110 to the damaged region 104) and distortion-corrected (using properties of the camera optics). These images may also be stored in database 1002.

In another embodiment, analysis workstation 1004 includes a modeling application 1008 that is able to process the data for the damaged region 104 for finite element analysis. The modeling application 1008 is able to access database 1002 to retrieve the data for the damaged region 104 of object 102. The modeling application 1008 then processes the data for the damaged region 104 to build a finite element model for object 102. The finite element model will take into consideration the effects of the damaged region 104 on object 102, such as stresses and strains. The maintenance crew can therefore use the finite element model of object 102 in accessing the severity of the damage, and selecting repair processes for object 102.

System 1000 may also include the LPS 110 that was used to collect the data for the damaged region 104. LPS 110 may be used to project an outline of the damaged region 104 on object 102. To do so, controller 116 of LPS 110 may access database 1002 to retrieve the data for the damaged region 104 of object 102. Controller 116 then processes the data for the damaged region 104, and controls laser ranging device 212 to emit a visible light beam onto object 102 based on the data for the damaged region 104. The light beam from laser ranging device 212 will show the boundary of the damaged region 104 as it was previously measured. This is especially beneficial when the damaged region 104 was measured in the past, and a maintenance crew is using LPS 110 to project the outline of prior damage onto object 102. Because the prior damage may have been fixed or painted over, LPS 110 can show the maintenance crew exactly where prior damage was located on object 102.

Any of the various elements shown in the figures or described herein may be implemented as hardware, software, firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, an element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments were described herein, the scope is not limited to those specific embodiments. Rather, the scope is defined by the following claims and any equivalents thereof.

The invention claimed is:

1. An apparatus comprising:
a measurement unit having a laser ranging device and a camera mounted on a gimbal assembly; and
a controller configured to calibrate the measurement unit with respect to a coordinate system of an object by controlling the measurement unit to perform measurements on reference points at known locations in the coordinate system of the object;
the controller is configured to capture an image of a damaged region on the object with the camera, to select target points around a boundary of the damaged region on the image, and to determine two-dimensional image coordinates for the target points on the image;
the controller is configured to determine aiming angles for aiming the laser ranging device at each of the target points based on the two-dimensional image coordinates;
the controller is configured to control motors of the gimbal assembly to aim the laser ranging device at the target points, to measure a distance to the target points with the laser ranging device, and to calculate three-dimensional coordinates for the target points in the coordinate system of the object based on the distance measurement and the two-dimensional image coordinates for the target points.

2. The apparatus of claim 1 wherein:
the controller is configured to select additional target points within the boundary of the damaged region on the image, to determine the two-dimensional image coordinates for the additional target points on the image, and to determine the aiming angles for aiming the laser ranging device at each of the additional target points based on the two-dimensional image coordinates;
the controller is configured to control the motors of the gimbal assembly to aim the laser ranging device at the additional target points, to measure a distance to the additional target points with the laser ranging device, and to calculate three-dimensional coordinates for the additional target points in the coordinate system of the object based on the distance measurement and the two-dimensional image coordinates for the additional target points.

3. The apparatus of claim 1 wherein:
the controller is configured to display the image of the damaged region to a user through a user interface, and to receive input from the user manually selecting the target points around the boundary of the damaged region on the image.

4. The apparatus of claim 1 wherein:
the controller is configured to process the image of the damaged region using an edge detection application to automatically select the target points around the boundary of the damaged region.

5. The apparatus of claim 1 wherein to calibrate the measurement unit with respect to the coordinate system of the object:
the controller is configured to control the measurement unit to aim the laser ranging device at the reference points on the object, to measure a distance to the reference points with the laser ranging device, to determine the aiming angles for aiming the laser ranging device at the reference points, and to calculate three-dimensional coordinates for the measurement unit in the coordinate system of the object based on the distance measurements and the aiming angles for the reference points.

6. The apparatus of claim 1 wherein:
the controller is configured to convert the two-dimensional image coordinates for the target points into elevation and azimuth angles, and to control the motors of the gimbal assembly to aim the laser ranging device at the target points based on the elevation and azimuth angles.

7. The apparatus of claim 1 wherein:
the controller is configured to store the three-dimensional coordinates in a database.

8. The apparatus of claim 1 wherein:
the object comprises an aircraft.

9. A method for mapping a damaged region on an object, the method comprising:
calibrating a measurement unit with respect to a coordinate system of the object by performing measurements with the measurement unit on reference points at known locations in the coordinate system of the object, wherein the measurement unit includes a laser ranging device and a camera mounted on a gimbal assembly;
capturing an image of the damaged region with the camera;
selecting target points around a boundary of the damaged region on the image;
determining two-dimensional image coordinates for the target points on the image;
determining aiming angles for aiming the laser ranging device at each of the target points based on the two-dimensional image coordinates;
controlling motors of the gimbal assembly to aim the laser ranging device at the target points based on the aiming angles;
measuring a distance to the target points with the laser ranging device; and
calculating three-dimensional coordinates for the target points in the coordinate system of the object based on the distance measurement and the two-dimensional image coordinates for the target points.

10. The method of claim 9 further comprising:
selecting additional target points within the boundary of the damaged region on the image;
determining the two-dimensional image coordinates for the additional target points on the image;
determining the aiming angles for aiming the laser ranging device at each of the additional target points based on the two-dimensional image coordinates;
controlling the motors of the gimbal assembly to aim the laser ranging device at the additional target points;
measuring a distance to the additional target points with the laser ranging device; and
calculating three-dimensional coordinates for the additional target points in the coordinate system of the object based on the distance measurement and the two-dimensional image coordinates for the additional target points.

11. The method of claim 9 wherein selecting target points around the boundary of the damaged region comprises:
displaying the image of the damaged region to a user through a user interface; and
receiving input from the user manually selecting the target points around the boundary of the damaged region on the image.

12. The method of claim 9 wherein selecting target points around the boundary of the damaged region comprises:
processing the image of the damaged region using an edge detection application to automatically select the target points around the boundary of the damaged region.

13. The method of claim 9 wherein calibrating the measurement unit into the coordinate system of the object comprises:
aiming the laser ranging device at the reference points on the object;
measuring a distance to the reference points with the laser ranging device;
determining the aiming angles for aiming the laser ranging device at the reference points; and
calculating three-dimensional coordinates for the measurement unit in the coordinate system of the object based on the distance measurements and the aiming angles for the reference points.

14. The method of claim 9 wherein controlling the motors of the gimbal assembly to aim the laser ranging device at the target points based on the aiming angles comprises:
converting the two-dimensional image coordinates for the target points into elevation and azimuth angles; and
controlling the motors of the gimbal assembly to aim the laser ranging device at the target points based on the elevation and azimuth angles.

15. The method of claim 9 further comprising:
storing the three-dimensional coordinates in a database.

16. The method of claim 9 wherein:
the object comprises an aircraft.

17. A non-transitory computer readable medium embodying programmed instructions which, when executed by a processor, are operable for performing a method of mapping a damaged region on an object, the method comprising:
calibrating a measurement unit with respect to a coordinate system of the object by performing measurements with the measurement unit on reference points at known locations in the coordinate system of the object, wherein the measurement unit includes a laser ranging device and a camera mounted on a gimbal assembly;
capturing an image of the damaged region with the camera;

selecting target points around a boundary of the damaged region on the image;

determining two-dimensional image coordinates for the target points on the image;

determining aiming angles for aiming the laser ranging device at each of the target points based on the two-dimensional image coordinates;

controlling motors of the gimbal assembly to aim the laser ranging device at the target points based on the aiming angles;

measuring a distance to the target points with the laser ranging device; and calculating three-dimensional coordinates for the target points in the coordinate system of the object based on the distance measurement and the two-dimensional image coordinates for the target points.

* * * * *